United States Patent [19]
Abe et al.

[11] Patent Number: 5,671,744
[45] Date of Patent: Sep. 30, 1997

[54] ULTRASONIC DIAGNOSIS APPARATUS

[75] Inventors: Yasuhiko Abe; Ryoichi Kanda; Makoto Hirama, all of Otawara, Japan

[73] Assignee: Kabushiki Kaisha Toshiba, Kawasaki, Japan

[21] Appl. No.: 512,931

[22] Filed: Aug. 9, 1995

[30] Foreign Application Priority Data

Aug. 15, 1994 [JP] Japan .................................. 6-191533
Jul. 10, 1995 [JP] Japan .................................. 7-173398

[51] Int. Cl.$^6$ ............................................... A61B 8/00
[52] U.S. Cl. ............................................... 128/660.07
[58] Field of Search ............... 128/660.07, 660.08, 128/660.09, 661.01, 661.07, 661.08, 661.09, 661.1, 662.01; 364/413.25; 73/602, 625, 626, 861.25

[56] References Cited

U.S. PATENT DOCUMENTS

5,177,691  1/1993  Welles et al. ................ 364/413.25
5,261,280  11/1993 Matzuk ........................ 128/661.08

Primary Examiner—George Manuel
Attorney, Agent, or Firm—Finnegan, Henderson, Farabow, Garrett & Dunner, L.L.P.

[57] ABSTRACT

A reception signal containing phase information and amplitude information is obtained by scanning a cross section of a subject with an ultrasonic wave. An ultrasonic image is formed on the basis of the reception signal and displayed. A noise component is filtered from reception signals at respective points in the cross section. The reception signals, which have not been non-linear processed, i.e., have not been subjected to an image forming process, are filtered. Therefore, the suppression effect of suppressing an image of a portion which moves at a relatively low speed and the emphasis effect of emphasizing an image a portion which moves at a relatively high speed can be improved as compared to the conventional art in which an ultrasonic image after non-linear process is filtered.

15 Claims, 8 Drawing Sheets

FIG. 16

ULTRASONIC DIAGNOSIS APPARATUS

BACKGROUND OF THE INVENTION

1. Field of the Invention

The present invention relates to an ultrasonic diagnosis apparatus for producing an ultrasonic image based on at least one of phase information and amplitude information contained in a reception signal obtained by scanning a cross section of a subject with an ultrasonic wave.

2. Description of the Related Art

To produce a tomographic image (B mode image) showing a tissue distribution, two linear processes of a reception signal, i.e., amplitude detection and logarithmic compression, are required. An ultrasonic wave radiated to a subject reflects at a boundary of an acoustic impedance. The intensity of reflection is proportional to a difference between acoustic impedances. Considering a transmission ultrasonic wave as a carrier wave, a reflection phenomenon is equivalent to an amplitude modulation. Hence, tissue information can be picked up by detecting an amplitude of a reception signal. To detect an amplitude, non-linear square-law detection is employed, since the amplitude of a reception signal is very small. Logarithm compression is to compress a dynamic range of a reception signal as great as, for example, $2^{20}$, into a dynamic range of a relatively small circuit, practically, a dynamic range of a monitor.

Figure 1:
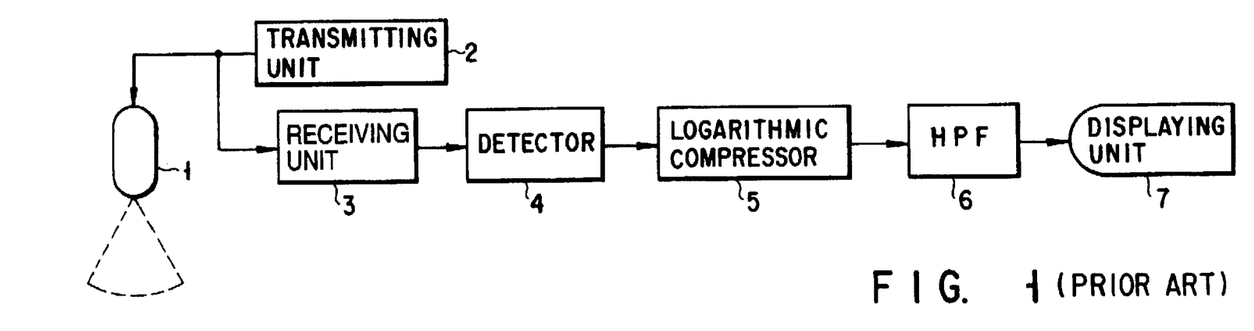
FIG. 1 is a block diagram showing a structure of a conventional ultrasonic diagnosis apparatus.

In a specific ultrasonic image diagnosis, it is desirable that only a portion which moves at a relatively high speed (e.g., a cardiac muscle) be emphasized, whereas a portion which moves at a relatively low speed (e.g., a breast wall or a costa) be suppressed. For this reason, according to the conventional art, it is proposed that, as shown in FIG. 1, a high pass filter (HPF) 6 is arranged in a stage subsequent to a detector 4 and a logarithmic compressor 5, thereby attenuating a static echo component of a relatively low frequency and emphasizing a signal echo component of a relatively high frequency, from a change with time of digital signals corresponding to a plurality of sample points in a cross section.

However, since both the amplitude detection and the logarithmic compression are non-linear processes, satisfactory effects of attenuating a static echo component and emphasizing a signal echo component cannot be obtained.

SUMMARY OF THE INVENTION

An object of the present invention is to provide an ultrasonic diagnosis apparatus wherein a function of extracting a portion, which moves at a relatively high speed, can be improved.

An ultrasonic diagnosis apparatus comprising: scanning means for scanning repeatedly a cross section of a subject with an ultrasonic wave to obtain reception signals, the reception signals containing phase information and amplitude information; image forming means for forming ultrasonic images based on at least one of the phase information and the amplitude information contained in the reception signals; display means for displaying sequentially the ultrasonic images; and filter means, arranged between the receiving means and the image forming means, for filtering a noise component.

A reception signal containing phase information and amplitude information is picked up by scanning a cross section of a subject with an ultrasonic wave. An ultrasonic image is formed on the basis of the reception signal and displayed. A noise component is filtered from reception signals at respective points in the cross section. Reception signals, which have not been non-linear processed, i.e., have not been subjected to an image forming process, are filtered. Therefore, a component of a stationary tissue which moves at a relatively low speed (e.g., a breast wall or a costa) can be eliminated and the function of extracting a heart signal component can be improved as compared to the conventional art in which an ultrasonic image after non-linear process is filtered.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

DETAILED DESCRIPTION OF THE PREFERRED EMBODIMENTS

Embodiments of the present invention will be described with reference to the accompanying drawings. In the following description, a sector electronic scanning system is employed as the scanning system. However, another scanning systems, such as a linear electronic scanning system or a convex scanning system, can also be employed.

(First Embodiment)

Figure 2:
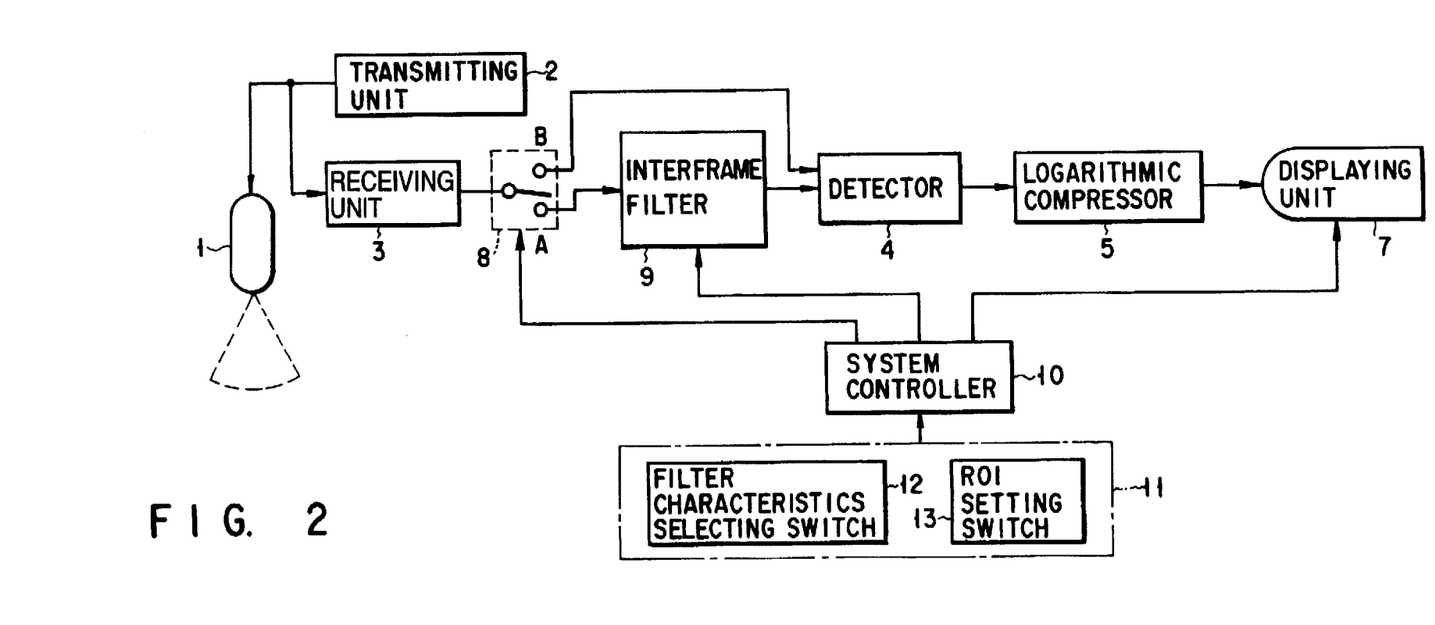
FIG. 2 is a block diagram showing a structure of an ultrasonic diagnosis apparatus according to a first embodiment of the present invention.

FIG. 2 shows a structure of an ultrasonic diagnosis apparatus according to a first embodiment of the present invention. A plurality of piezoelectric elements for converting a mechanical vibration to an electric signal, and vice versa, are arranged at a distal end of an ultrasonic probe 1. The ultrasonic probe 1 is connected to a transmitting unit 2 in a transmitting period and to a receiving unit 3 in a receiving period. The receiving unit 2 includes a clock generator, a frequency divider, a distributor, a transmission delay circuit and a pulser (which are not shown in the drawings). A clock pulse generated by the clock generator is frequency-divided by the frequency divider into rate pulses of, for example, 6 KHz. The rate pulses output from the frequency divider are distributed by the distributor to a required number of channels. The rate pulses output from the distributor are given different delay times for the respective channels by the transmission delay circuit. The delay time of each channel is determined by a delay time required for focusing an ultrasonic wave to a beam and a delay time in accordance with the transmission direction in which the ultrasonic beam is transmitted. By changing the latter delay time, it is possible to scan a fan-shaped cross section of a subject by means of the ultrasonic beam. The rate pulse for each channel, output from the transmission delay circuit, is supplied as a trigger to a pulser for the corresponding channel. The pulser applies a pulse voltage to the piezoelectric element of the corresponding channel at a timing at which the pulser receives the rate pulse. As a result, an ultrasonic beam is emitted from the ultrasonic probe 1 in a direction corresponding to the delay time. One piezoelectric element or a plurality of adjacent piezoelectric elements correspond to one channel.

An ultrasonic wave reflects at a boundary of an acoustic impedance in a subject. The reflected wave is received by the piezoelectric elements and converted to an electric signal (voltage signal). The electric signal of the piezoelectric elements in every channel is picked up by the receiving unit 3. The receiving unit 3 includes a preamplifier, an analog-to-digital converter, a reception delay circuit and an adder (which are not shown in the drawings). The preamplifier, the analog-to-digital converter, the reception delay circuit and the adder are linear circuits. The preamplifier amplifies the electric signal in every channel. The analog-to-digital converter samples the amplified electric signal of each channel at a sampling frequency corresponding to 0.5 mm intervals for one scanning line, and converts the sampled signal to a digital signal for each sampling point. Digital signals are given different delay times for the respective channels by the reception delay circuit. The delay time of each channel is determined by a delay time required for focusing an ultrasonic wave to a beam and a delay time in accordance with the reception direction in which the reflected wave is received. In general, the reception direction is the same as the transmission direction. The digital signals of the respective channels output from the reception delay circuit are added by the adder. As a result, a reception signal is obtained, in which a reflection component in a specific direction is emphasized. The reception signal contains amplitude information, which reflects the difference in acoustic impedance between tissues, and phase information, which reflects movement (speed of movement) of a reflection body.

A reception signal output from the receiving unit 3 is transmitted to a detector 4. The detector 4 detects an amplitude of the amplitude-modulated reception signal. As a result, amplitude information is picked up. A non-linear square-law detecting system is employed as the detector 4, since (the amplitude of?) a reception signal is very small. A signal output from the detector 4 is supplied to a logarithmic compressor 5 of a non-linear circuit. The logarithmic compressor 5 compresses a dynamic range of a reception signal as great as, for example, $2^{20}$, into a dynamic range of a relatively small circuit, practically, a dynamic range which can be treated by a display unit 7, and generates image data of the B mode, which reflects the texture distribution. The detector 4 and the logarithmic compressor 5 are defined as image generating means. The image generated by the image generating means only reflects amplitude information, not phase information. In this respect, the image data should completely be distinguished from the reception signal containing both information. The reception signal, containing both amplitude information and phase information, is defined as a signal which has not been subjected to a non-linear process.

The image data is supplied to the display unit 7 and visually displayed as a B mode image at various densities.

An interframe filter 9 is arranged before the image forming means including the non-linear circuit, and between the receiving unit 3 and the detector 4. A selector 8, arranged between the receiving unit 3 and the detector 4, selects whether the interframe filter 9 is bypassed or not. In other words, it selects one of a first state in which a reception signal is supplied from the receiving unit 3 through the interframe filter 9 to the detector 4 and a second state in which a reception signal is supplied directly to the detector 7 from the receiving unit 3.

Figure 5A:
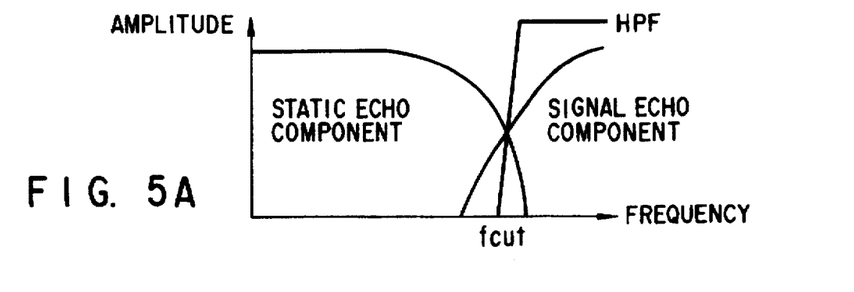
FIGS. 5A and 5B are diagrams for explaining filter characteristics.
Figure 5B:
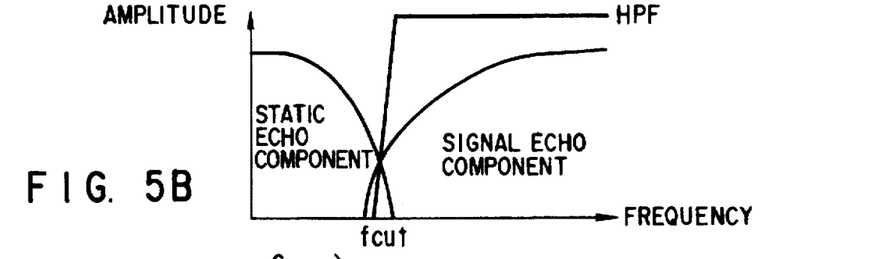

The interframe filter 9 is a high-pass digital filter for filtering a low-frequency component (noise component) and allowing passage of a high-frequency component (signal component) contained in a change with time (time signal) of digital signals at the respective sample points. The interframe filter circuit 9 is operable at any one of a plurality of filter characteristics. A filter characteristic is defined as a cut-off frequency $f_{cut}$ as shown in FIGS. 5A and 5B.

A system controller 10 is connected to a console 11. The console 11 comprises a plurality of switches including a filter characteristics selecting switch 12, which allows the operator to select a filter characteristic of the interframe filter 9, and a region of interest (ROI) setting switch 13, which allows the operator to set a region of interest ROI in a displayed B mode image. The console 11 also comprises a mouse, a keyboard, and so on.

The system controller 10 controls the interframe filter 9 so that the filter characteristic selected by the filter characteristics selecting switch 12 can be applied. The system controller 10 also controls the selector 8, so that the first state is set in a period when a reception signal in the region of interest is output from the receiving unit 3, and the second state is set in a period when a reception signal in a region other than the region of interest is output from the receiving unit 3.

Figure 3:
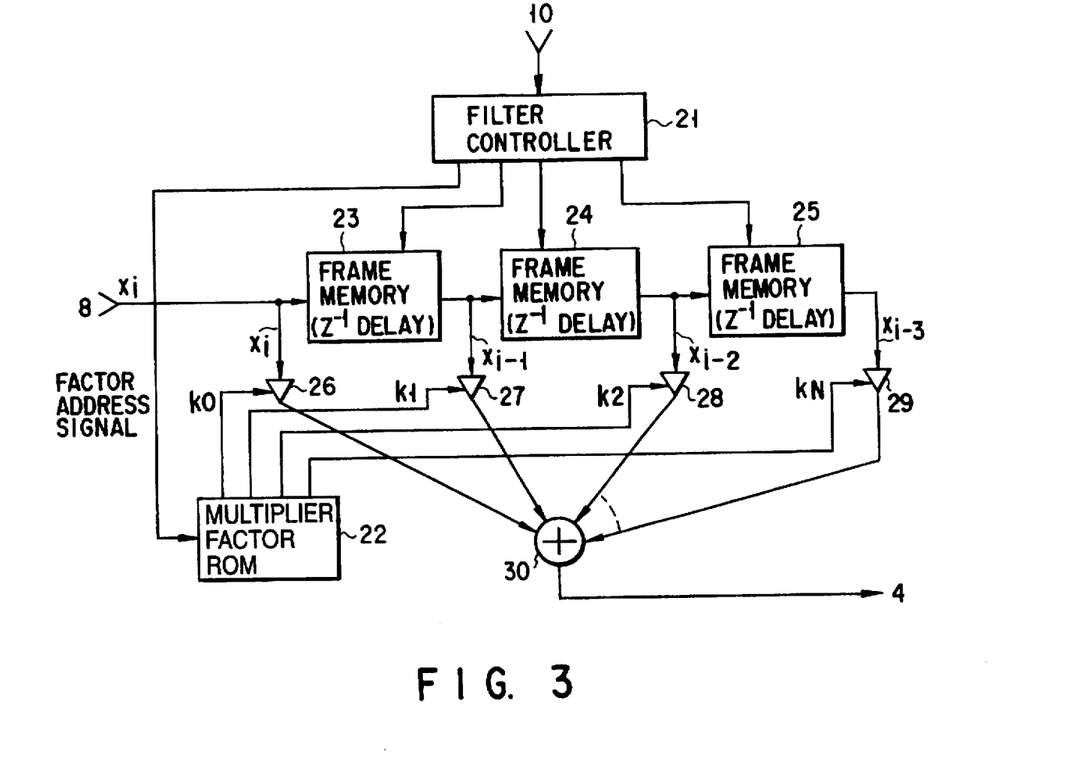
FIG. 3 is a block diagram showing a structure of the interframe filter shown in FIG. 2.
Figure 4:
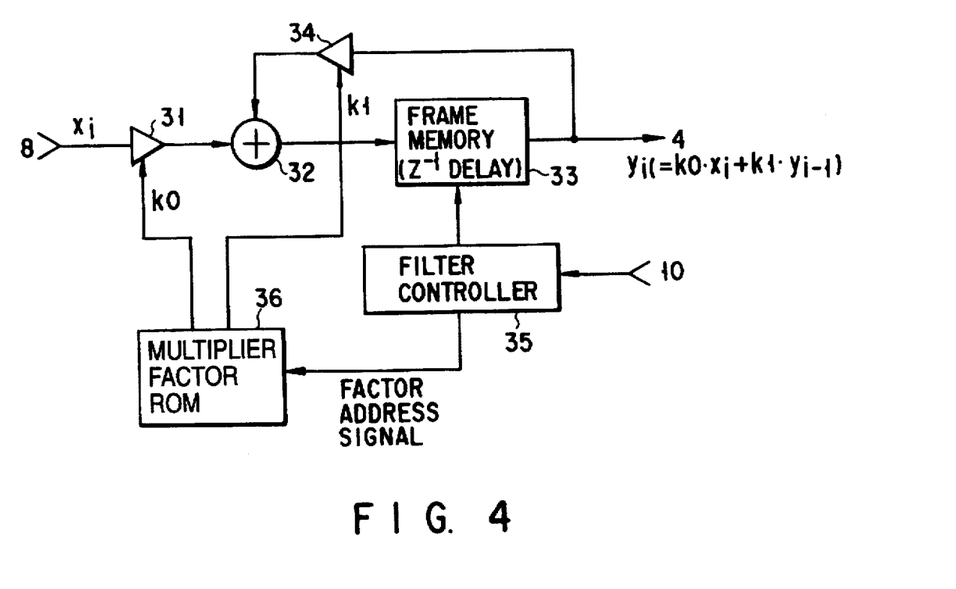
FIG. 4 is a block diagram showing another structure of the interframe filter shown in FIG. 2.

FIGS. 3 and 4 are block diagrams showing structures of the interframe filter 9. FIG. 3 shows a digital filter of FIR type (non-recursive type) and FIG. 4 shows a digital filter of IIR type (recursive type). Either the FIR type or the IIR type can be employed as the interframe filter 9.

The interframe filter 9 of the FIR type is constituted as shown in FIG. 3, using a filter controller 21 as a control center. It is assumed that the degree of the transfer function is 3. Three frame memories 23 to 25, corresponding to the degree, function as delay devices for delaying a scan at the frame frequency $Z^{-1}$ under write/read control of the filter controller 21. The frame memories 23 to 25 are connected to form multiple stages, so as to simultaneously supply a current digital signal $x_i$, a digital signal $x_{i-1}$ at one frame before, a digital signal $x_{i-2}$ at two frames before, and a digital signal $x_{i-3}$ at three frames before, with respect to the same sampling point, to multipliers 26, 27, 28 and 29, respectively. The results of the multiplication are added together by an adder 30. The result of the addition is output as a signal $y_i$ in which a low-frequency component is attenuated. Multiplier factors $k_0$, $k_1$, $k_2$ and $k_3$ are respectively supplied to the multipliers 26 to 29 from a multiplier factor ROM 22. A filter characteristic is determined in accordance with the combination of the multiplier factors $k_0$, $k_1$, $k_2$ and $k_3$. Various combinations of the multiplier factors, in a range of maintaining the high-pass type, are prestored in the multiplier factor ROM 22. The filter characteristic of the interframe filter 9 varies depending on the combination of the multiplier factors read from the multiplier factor ROM 22. The system controller 10 supplies, to the filter controller 21, identification information for identifying the filter characteristic selected by the filter characteristics selecting switch 12 or a factor address itself. The filter controller 21 supplies the factor address to the multiplier factor ROM 22. Four multiplier factors stored in portions corresponding to the factor addresses are read from the multiplier factor ROM 22 to the respective multipliers 26 to 29.

The interframe filter 9 of the IIR type is constituted as shown in FIG. 4, using a filter controller 35 as a control center. A digital signal $x_i$ output from the receiving unit 3 is supplied through a multiplier 31 to an adder 32. An output of the adder 32 is connected to a frame memory 33, which functions as a delay device for delaying a scan at the frame frequency $Z^{-1}$ under write/read control of the filter controller 35, so that an output signal $y_{i-1}$, which has been output one frame period $Z^{-1}$ before, recurs to the adder 32 through the multiplier 34. Multiplier factors $k_0$ and $k_1$ are respectively supplied to the multipliers 31 and 34 from a multiplier factor ROM 36. A filter characteristic is determined in accordance with the combination of the multiplier factors $k_0$ and $k_1$. Various combinations of the multiplier factors, in a range of maintaining the high=pass type, are prestored in the multiplier factor ROM 36. The filter characteristic of the interframe filter 9 varies depending on the combination of the multiplier factors read from the multiplier factor ROM 36. The system controller 10 supplies, to the filter controller 35, identification information for identifying the filter characteristic selected by the filter characteristics selecting switch 12 or a factor address itself. The filter controller 35 supplies the factor address to the multiplier factor ROM 36. Two multiplier factors stored in portions corresponding to the factor addresses are read from the multiplier factor ROM 36 to the respective multipliers 31 to 34.

Figure 6A:
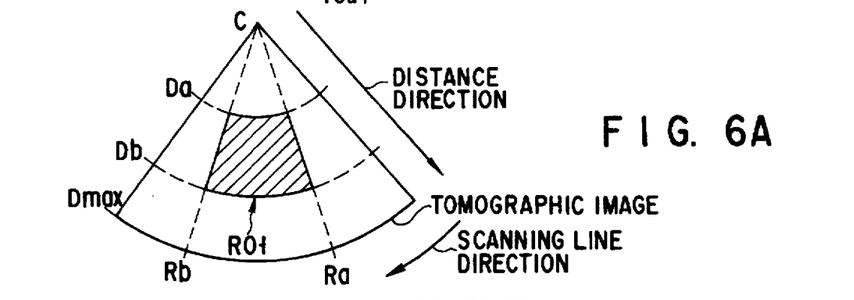
FIGS. 6A to 6C are diagrams for explaining an operation of the selector shown in FIG. 2.
Figure 6B:
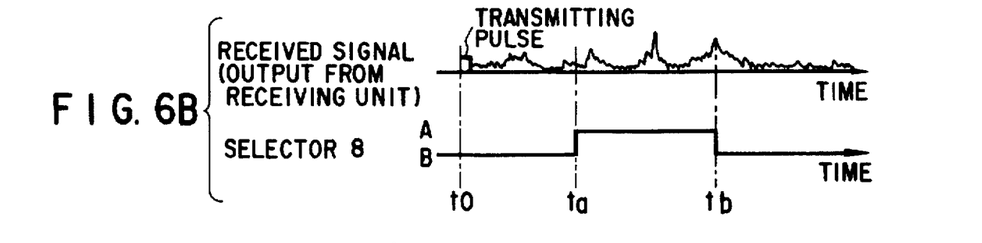
Figure 6C:
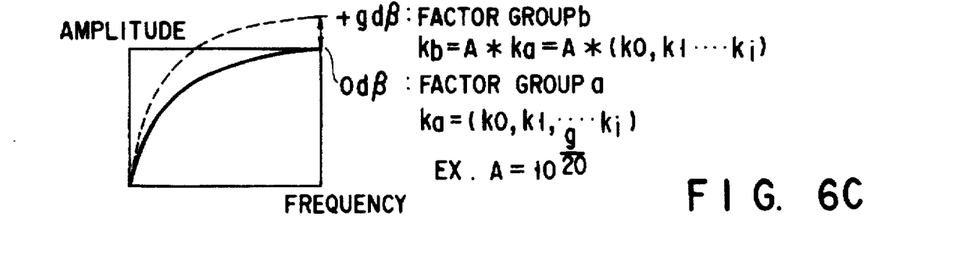

An operation of the above embodiment will now be described. FIGS. 6A to 6C are diagrams for explaining switching operations of the selector 8. The ROI setting switch 13 is operated by the operator. As a result, the region-of-interest ROI enclosed by two scanning lines $R_a$ and $R_b$ and two contour lines $D_a$ and $D_b$ is set, as shown in FIG. 6A.

Digital signals at a plurality of sample points located on the same scanning line are sequentially output from the receiving unit 3, beginning with the signal at the shallowest point, i.e., at the shortest distance from the probe 1. FIG. 6B is a diagram for explaining a switching operation by means of the selector 8. While a digital signal at a sampling point out of the ROI is output from the receiving unit 3, the selector 8 is maintained in the second state under control of the system controller 10, and the digital signal bypasses the interframe filter 9 and directly supplied to the detector 4. While a digital signal at a sampling point within the ROI is output from the receiving unit 3, the selector 8 is maintained in the first state under control of the system controller 10, and the digital signal is supplied to the detector 4 through the interframe filter 9. The latter period is determined to be a period between a time $t_a$, when the time corresponding to twice the depth $D_a$ at the shallowest point of the ROI has elapsed, and a time $t_b$, when the time corresponding to twice the depth $D_b$ at the deepest point of the ROI has elapsed, assuming that the time when an ultrasonic pulse is emitted is $t_0$.

With the above operation, the detector 4 and the logarithmic compressor 5 generate, in the ROI, image data in which a portion moving at a relatively low speed is suppressed and a portion moving at a relatively high speed is emphasized, and outside the ROI, normal image data with no suppression or emphasis. These display modes produce the following effect. Assume that all the region in the cross section is subjected to an interframe filter process. With the interframe filter process, a tissue distribution at a portion which moves at a relatively low speed (a low speed portion) is suppressed, whereas a tissue distribution at a portion which moves at a relatively high speed (a high speed portion) is emphasized. It follows that the tissue distribution of the high speed portion can be satisfactory observed, whereas the tissue distribution of the low speed portion cannot be recognized. This is very disadvantageous in diagnosis. However, in the above embodiment, since the tissue distribution of the low speed portion outside the ROI can be observed, the tissue distribution of the low speed portion in the ROI can be analogized to a certain extent.

A high speed portion can be further emphasized by controlling the gain within the ROI to a value greater than that in the region out of the ROI. This gain control can be achieved by selecting one of a first factor group having a normal gain $0_{dB}$ and a second factor group having a gain $g_{dB}$ ($g>0$) stored in, for example, the multiplier factor ROM 22, depending on whether inside or outside the ROI (see FIG. 6C).

Figure 7:
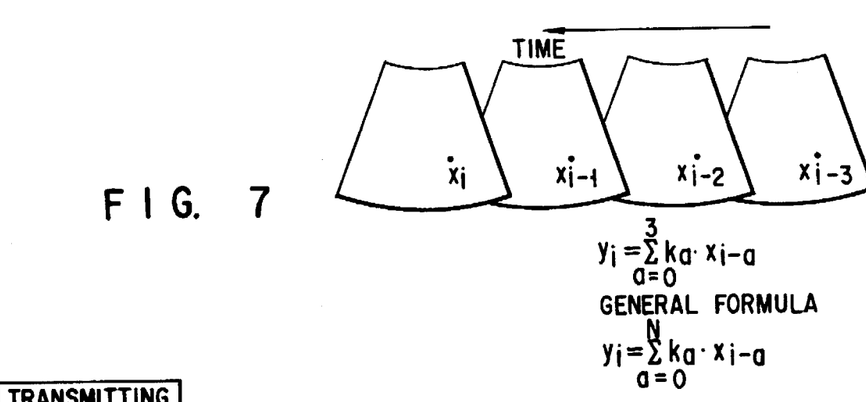
FIG. 7 is a diagram for explaining an operation of the interframe filter circuit.

FIG. 7 is a diagram for explaining an interframe filter process. In the following description, the interframe filter circuit 9 is assumed to be a digital filter of FIR type. The filter controller 21 controls read/write operations of the three frame memories 23 to 25 based on a frame renewal signal (frame synchronizing signal) output from the system controller 10. As a result, the frame memories 23 to 25 function as delay devices for delaying a scan at the frame frequency $Z^{-1}$. A current digital signal $x_i$, a digital signal $x_{i-1}$ one frame before, a digital signal $x_{i-2}$ two frame before, and a digital signal $x_{i-3}$ three frame before, with respect to the same sampling point, are simultaneously supplied to multipliers 26, 27, 28 and 29, respectively, and multiplied with the multiplier factors $k_0$, $k_1$, $k_2$ and $k_3$. The results of the multiplication $k_0 \cdot x_i$, $k_1 \cdot x_{i-1}$, $k_2 \cdot x_{i-2}$ and $k_3 \cdot x_{i-3}$ are added together by the adder 30. The result of the addition is output as a digital signal $y_i$ in which a low-frequency component, lower than the cut-off frequency $f_{cut}$ corresponding to the filter characteristic, is attenuated.

A high-pass filter process is performed with respect to a reception signal, which has been subjected to the linear process of the receiving unit 3 and has not been subjected to the non-linear process of the detector 4 and the logarithmic compressor 5. As compared to the conventional art in which the non-linear processed signal processed by the detector 4 and the logarithmic compressor 5 is subjected to a high-pass filter process, the suppression effect of the low speed portion and the emphasis effect of the high speed portion can be improved, thereby improving the function of extracting a signal component of the heart.

An operation of selecting a filter characteristic will be described. The system controller 10 supplies, to the filter controller 21, identification information for identifying the filter characteristic selected by the filter characteristics selecting switch 12 or a factor address itself. The filter controller 21 supplies the factor address to the multiplier factor ROM 22 at a timing on the basis of the frame renewal signal supplied from the system controller 10. Four multiplier factors stored in portions corresponding to the factor addresses are read from the multiplier factor ROM 22 to the respective multipliers 26 to 29. Thus, a selected filter characteristic is achieved. In this manner, the most suitable filter characteristic can be set in accordance with the movement speed of a portion to be diagnosed, and an unnecessary low-frequency component can be satisfactorily attenuated.

Figure 8:
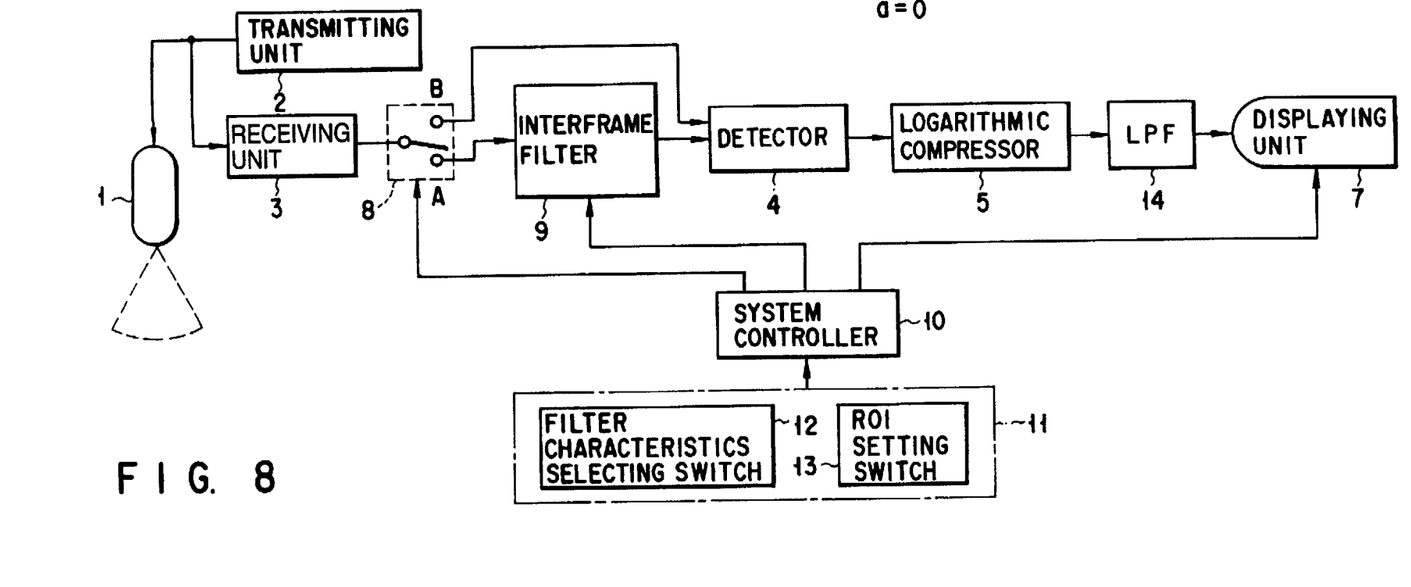
FIG. 8 is a block diagram showing a modification of the ultrasonic diagnosis apparatus of the first embodiment.

The above embodiment can be modified as follows. As shown in FIG. 8, a low-pass filter (LPF) 14 is provided between the logarithmic compressor 5 and a display unit 7 in the same manner as in the conventional art, so that the non-linear processed image data can be subjected to a filter process between frames. In this case, a low-frequency static echo component is attenuated by the interframe filter 9, and at the same time, an image is smoothed by the low-pass filter 14.

(Second Embodiment)

In the second embodiment, filter characteristics, i.e., cut-off frequencies, are sequentially varied in accordance with the time phase of beats, noting that for example, a cardiac muscle, moves at a relatively low speed in a diastole and at a relatively high speed in a systole.

Figure 9:
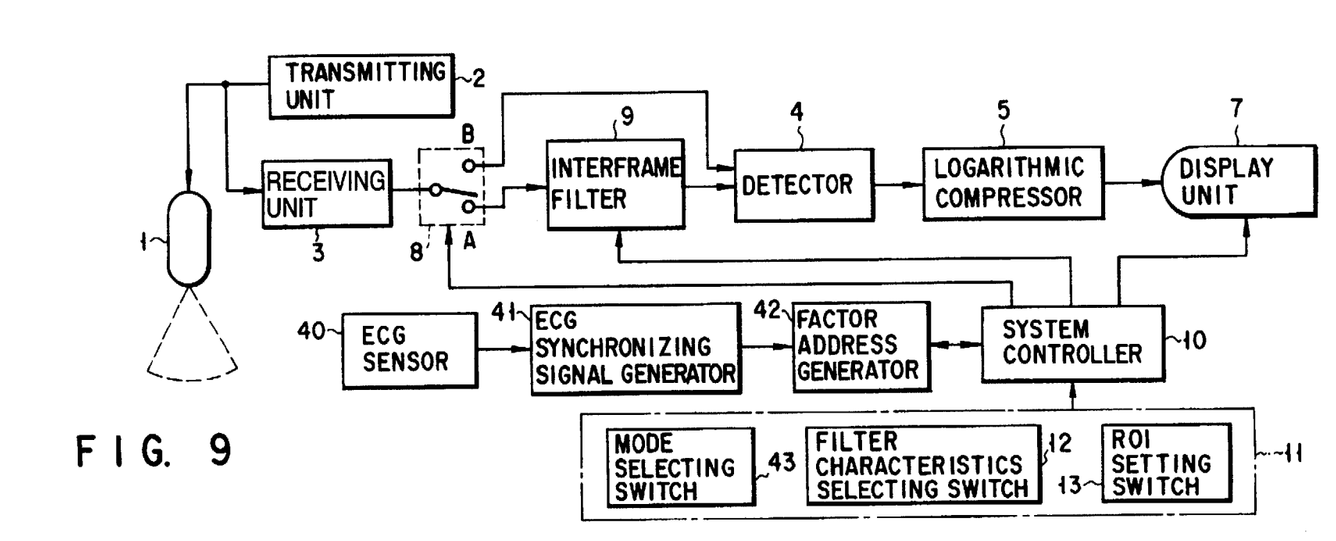
FIG. 9 is a block diagrams showing a structure of an ultrasonic diagnosis apparatus according to a second embodiment of the present invention.
Figure 11:
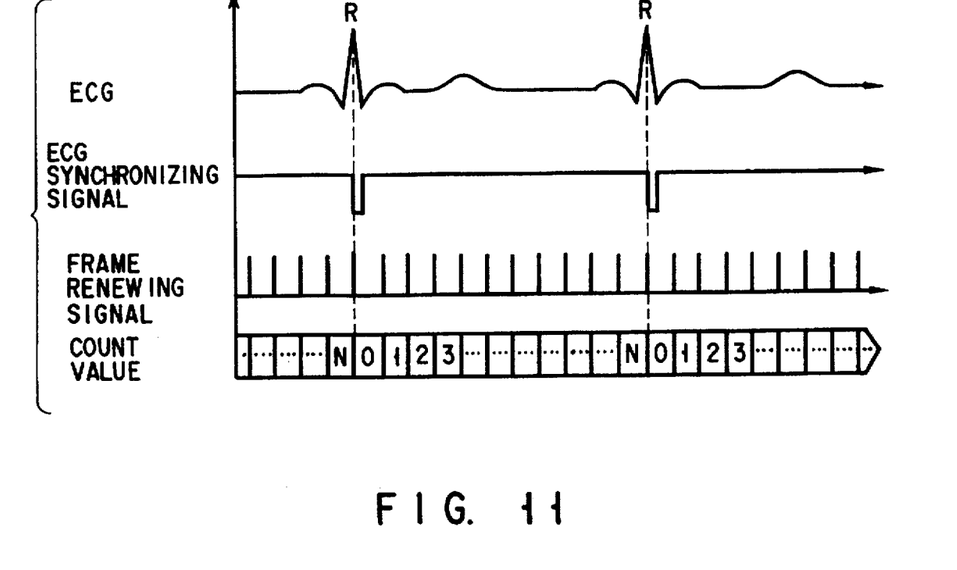
FIG. 11 is a diagram showing a sequential change of a cut-off frequency in first and second modes.

FIG. 9 is a block diagrams showing a structure of an ultrasonic diagnosis apparatus according to a second embodiment of the present invention. In FIG. 9, the same components as those shown in FIG. 2 are identified with the same reference numerals, and descriptions thereof will be omitted. An electrocardiogram (ECG) signal related to the subject, measured by an ECG sensor (electrocardiograph) 40, is supplied to an ECG synchronizing signal generator 41. The ECG synchronizing signal generator 41 generates an ECG synchronizing signal at a timing of a spiky R wave in the ECG signal (see FIG. 11). A factor address generator 42 generates an address corresponding to a time phase of the beats, i.e., a lapse of time after the timing at which the ECG synchronizing signal is received. The factor address output from the factor address generator 42 is supplied to the interframe filter 9 through the system controller 10. The filter characteristic corresponding to the factor address is achieved by the interframe filter 9. Since the factor address output from the factor address generator 42 varies in accordance with the time phase of beats, the filter characteristic of the interframe filter 9 sequentially varies also in accordance with the time phase of beats. As a result, the filter process at the most suitable filter characteristic can be performed in accordance with the time phase of the beats.

The mode address generator 42 has first and second modes. In the first mode, the factor address generator 42 outputs a factor address in accordance with the time phase of the beats such that the filter characteristic of the interframe filter 9 sequentially varies in a first pattern. In the second mode, the factor address generator 42 outputs a factor address in accordance with the time phase of the beats such that the filter characteristic of the interframe filter 9 sequentially varies in a second pattern. Although the first and second patterns are different from each other, both patterns satisfy the condition that the filter characteristic (cut-off frequency) in a systole is higher than that in a diastole. Selection of the modes is achieved by an operation of a mode selecting switch 43 in the console 11.

Figure 10:
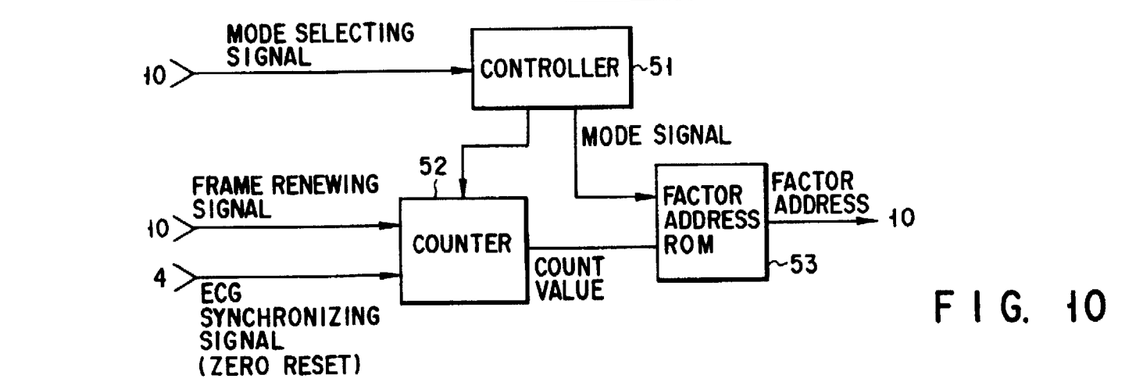
FIG. 10 is a block diagram showing a structure of the factor address generator shown in FIG. 9.

FIG. 10 is a block diagram showing a structure of the factor address generator 42. A frame renewal signal is supplied to a counter 52 from the system controller 10. An ECG synchronizing signal is also supplied to the counter 52 as a zero reset signal from the ECG synchronizing signal generator 41. The frame renewal signals are repeatedly supplied in a constant frame period every time a scan for one frame has been completed (see FIG. 11). The counter 52 counts the number of frame renewal signals repeatedly supplied, and resets the count value to zero when the ECG synchronizing signal is supplied thereto. As a result, the count value corresponds to the time phase of the beats (see FIG. 11). A count value signal is supplied as an address signal to a factor address ROM 53 along with a mode signal which a controller 51 outputs upon reception of a mode selecting signal from the system controller 10. A factor address signal corresponding to the count value signal and the mode signal, i.e., a factor address signal corresponding to the mode and the time phase, is read out from the factor address ROM 53.

Figure 12:
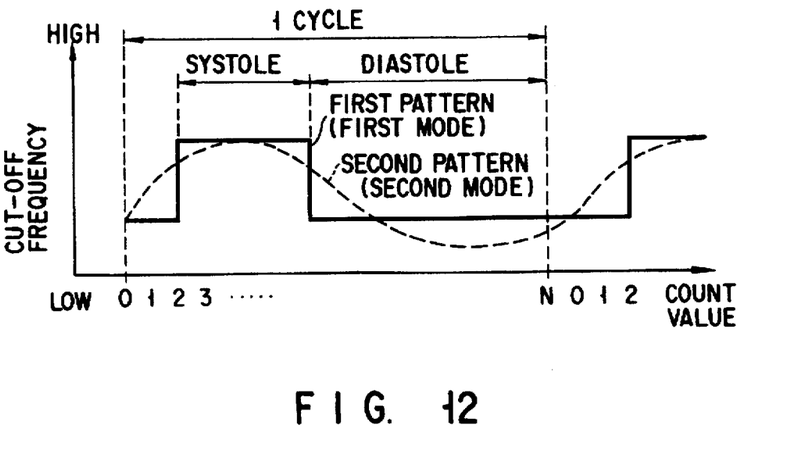
FIG. 12 is a diagram for explaining a counting operation of a counter.

In the first mode, a factor address, corresponding to the mode and the time phase of the beats, is read from the factor address generator 42, so that the filter characteristic (cut-off frequency) of the interframe filter 9 is sequentially changed in the first pattern, as shown in FIG. 12. In the second mode, a factor address, corresponding to the mode and the time phase of the beats, is read from the factor address generator 42, so that the filter characteristic (cut-off frequency) of the interframe filter 9 is sequentially changed in the second pattern, as shown in FIG. 12.

According to the second embodiment, the following advantage can be obtained in addition to the advantage of the first embodiment. The filter characteristic, i.e., the cut-off frequency, is sequentially changed in accordance with the time phase of beats of the heart. As a result, a filter process at the most suitable filter characteristic, corresponding to the time phase of beats, is performed, so that only a portion which moves at a relatively high speed (e.g., a cardiac muscle) is satisfactorily emphasized, whereas a portion which moves at a relatively low speed (e.g., a breast wall or a costa) is suppressed. Further, the optimal pattern of the sequential change of the filter characteristic can be suitably selected.

(Third Embodiment)

Figure 13:
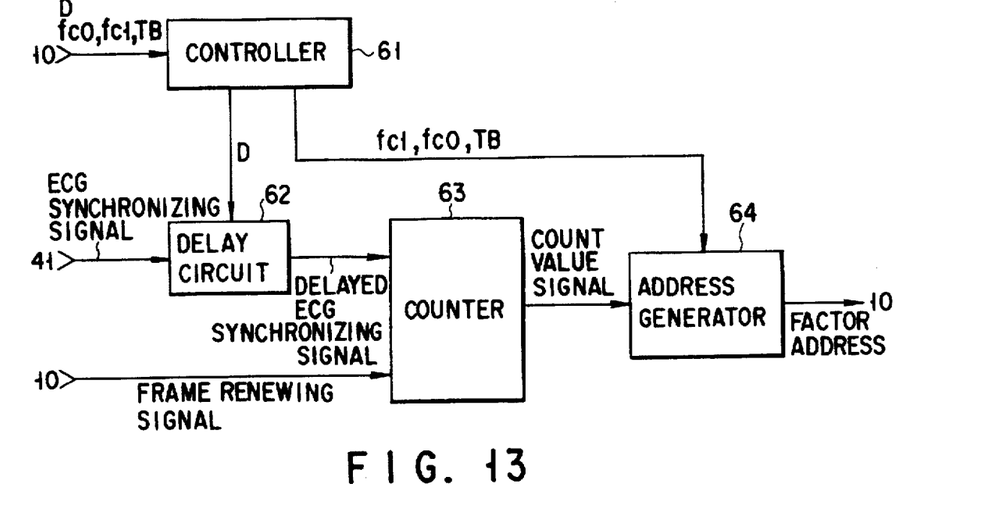
FIG. 13 is a diagram showing a structure of the main part of an ultrasonic diagnosis apparatus according to a third embodiment of the present invention.

FIG. 13 is a diagram showing a structure of the main part of an ultrasonic diagnosis apparatus according to a third embodiment of the present invention. An ECG synchronizing signal from the ECG synchronizing signal generator 41 is supplied to a counter 63 through a delay circuit 62. The delay circuit 62 provides the ECG synchronizing signal with a delay time D. The counter 63 counts the number of frame renewal signals supplied from the system controller 10, and resets the count value to zero upon reception of the ECG synchronizing signal from the delay circuit 62.

The controller 61 receives various data, such as a delay time D, a first cut-off frequency $f_{co}$, a second cut-off frequency $f_{c1}$ and a continued time $T_B$, from the system controller 10. The controller 61 sets the delay time of the delay circuit 62 to D. The controller 61 supplies the first cut-off frequency $f_{co}$, the second cut-off frequency $f_{c1}$ and the continued time $T_B$ to an address generator 64. The first cut-off frequency $f_{co}$ is lower than the second cut-off frequency $f_{c1}$. The address generator 64 outputs a first address signal corresponding to the first cut-off frequency $f_{co}$ in a first period having a time width of a continued time $T_B$, i.e., a lapse of time after the timing at which the ECG synchronizing signal is received from the delay circuit 62. In a second period, other than the first period, the address generator 64 outputs a second address signal corresponding to the second cut-off frequency $f_{c1}$.

The first period corresponds to a period in which the heart moves at a relatively low speed and the second period corresponds to a period in which the heart moves at a relatively high speed.

An address signal output from the address generator 64 is supplied to the interframe filter 9 through the system controller 10. As regards the characteristic of the interframe filter 9, the first cut-off frequency $f_{co}$ is set by the first address signal and the second cut-off frequency $f_{c1}$ is set by the second address signal.

Thus, in a period in which the heart moves at a relatively high speed, the lower first cut-off frequency $f_{co}$ is set, so that omission of a heart signal component can be prevented. In a period in which the heart moves at a relatively high speed, the higher second cut-off frequency $f_{c1}$ is set, so that a component relating to a static tissue, such as a breast wall or a costa, which moves at a relatively low speed, can be eliminated, thereby improving the function of extracting a heart signal component.

Figure 14:
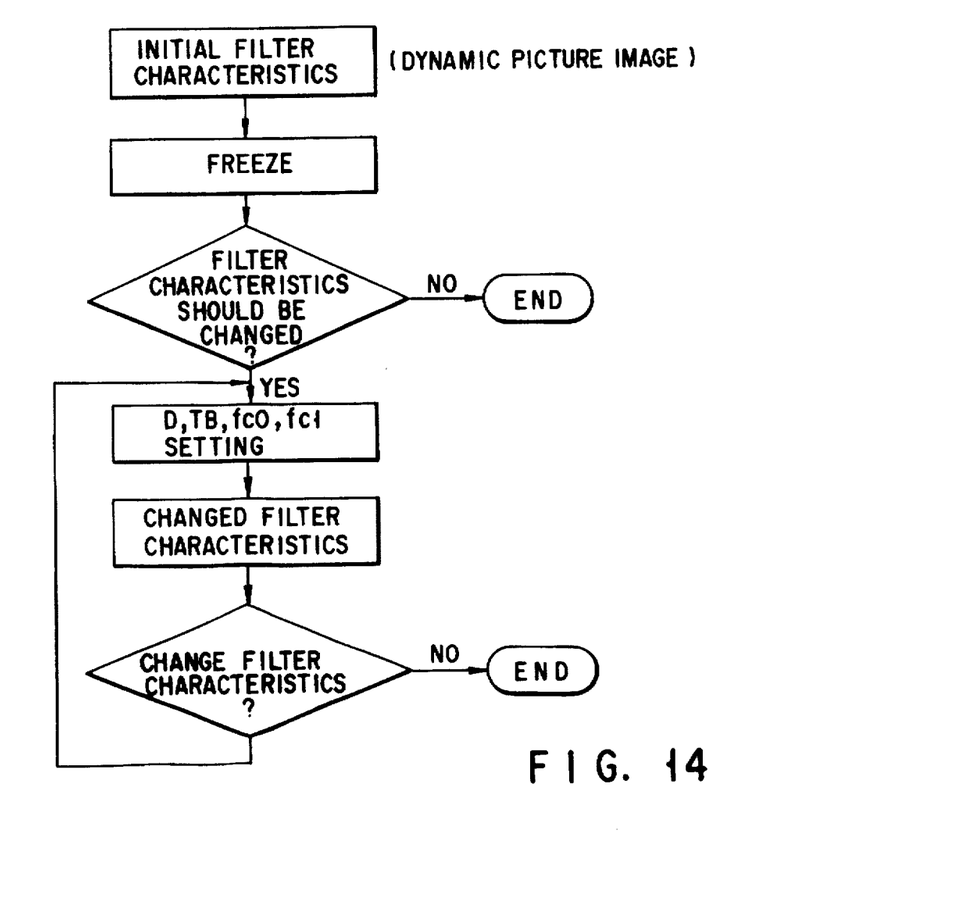
FIG. 14 is a diagram for explaining an operation of the third embodiment.

FIG. 14 is a flowchart showing an operation of the third embodiment. At first, the filter characteristic of the interframe filter 9 is set to an initial cut-off frequency. The initial cut-off frequency may be equivalent to the second cut-off frequency $f_{c1}$. In a state where the filter characteristic is fixed to the initial cut-off frequency, an image is displayed in real time (dynamic picture image display). The dynamic picture image display is stopped by a suitable operation of the console 11 by the operator, and specified image data is repeatedly read out from the image memory in the display unit 7. The specified image is an image which have been picked up in a period in which a cardiac muscle is stationary. As a result, the specified image is displayed in a frozen state.

The operator observes the specified image displayed. When the image of the stationary cardiac muscle can be observed satisfactory, the process is ended. When it is difficult to observe the image of the stationary cardiac muscle, the operation is changed to a filter characteristic change mode, in which the delay time D, the first cut-off frequency $f_{co}$, the second cut-off frequency $f_{c1}$ and the continued time $T_B$ are set by the operator.

Figure 15:
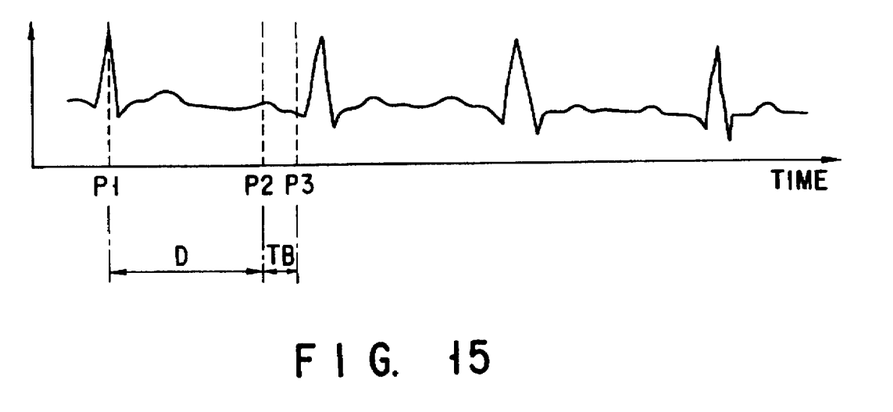
FIG. 15 is a diagram for explaining a method for setting a delay time D and a continued time $T_B$.

FIG. 15 shows an ECG waveform displayed on the display unit 7. A time phase $P_1$ of an R wave, a time phase $P_2$ at a start point of the period in which the heart moves at a relatively low speed, and a time phase $P_3$ at an end point of this period are designated on the ECG waveform by a suitable operation of the console 11 by the operator.

The system controller 11 obtains the delay time D as a period of time between the time phases $P_1$ and $P_2$, and the continued time $T_B$ as a period of time between the time phases $P_2$ and $P_3$. The obtained times D and $T_B$ are supplied to the controller 61. The delay time of the delay circuit 62 is set to D by the controller 61.

Figure 16:
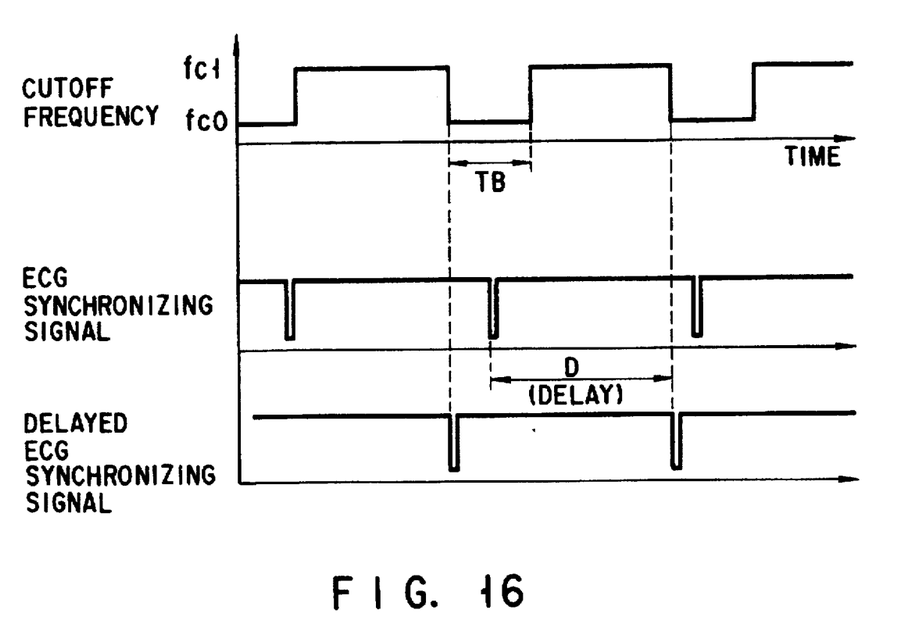
FIG. 16 is a timing chart showing a delay of an ECG synchronizing signal and a sequential change of a cut-off frequency.

FIG. 16 is a timing chart showing a delay of an ECG synchronizing signal and a sequential change of a cut-off frequency. An ECG synchronizing signal output from the ECG synchronizing signal generator 41 is synchronized with an R wave as a start point of a heart beat cycle. A delayed ECG synchronizing signal output from the delay circuit 62 is in synchronism with the start point of the first period in which the heart moves at a relatively low speed.

The address generator 64 outputs a first address signal corresponding to the first cut-off frequency $f_{co}$ in a first period having a time width of a continued time $T_B$, i.e., a lapse of time after the reception of the ECG synchronizing signal from the delay circuit 62. In a second period, other than the first period, the address generator 64 outputs a second address signal corresponding to the second cut-off frequency $f_{c1}$.

An address signal output from the address generator 64 is supplied to the interframe filter 9 through the system controller 10. As regards the characteristic of the interframe filter 9, the first cut-off frequency $f_{co}$ is set by the first address signal and the second cut-off frequency $f_{c1}$ is set by the second address signal.

In a period in which the heart moves at a relatively high speed, the lower first cut-off frequency $f_{co}$ is set, so that omission of a heart signal component can be prevented. In a period in which the heart moves at a relatively high speed, the higher second cut-off frequency $f_{c1}$ is set, so that a component relating to a static tissue, such as a breast wall or a costa, which moves at a relatively low speed, can be eliminated, thereby improving the function of extracting a heart signal component.

The present invention is not limited to the above embodiments, but can be variously modified. For example, it is possible to add a factor of the depth of a sample point to prepare a factor address, so that the filter characteristic can be varied depending on the depth.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An ultrasonic diagnosis apparatus comprising:

scanning means for repeatedly scanning a cross section of a subject with an ultrasonic wave to obtain echo signals, the echo signals containing phase information and amplitude information;

sampling means for sampling the echo signals at a predetermined time rate to obtain a time-series of echo signals, the time-series of the echo signals representing a time-change of reflection on a same point in the cross section;

filtering means for filtering the time-series of the echo signals to reduce a noise frequency component;

image forming means for forming ultrasonic images based on at least one of the phase information and the amplitude information contained in the filtered echo signals; and display means for sequentially displaying the ultrasonic images.

2. The ultrasonic diagnosis apparatus according to claim 1, wherein the sampling means samples the echo signals at a frame rate.

3. The ultrasonic diagnosis apparatus according to claim 2, wherein said scanning means includes digitizing means for digitizing the echo signals.

4. The ultrasonic diagnosis apparatus according to claim 1, wherein the filter means reduces a low frequency component as the noise components.

5. The ultrasonic diagnosis apparatus according to claim 4, wherein said filtering means have a variable cut-off frequency.

6. The ultrasonic diagnosis apparatus according to claim 5, further comprising filter control means for controlling said filtering means so that the cut-off frequency is sequentially varied in accordance with a time phase of heart beats.

7. The ultrasonic diagnosis apparatus according to claim 6, wherein said filter control means controls said filtering means so that the cut-off frequency in a time phase in which the heart moves at a relatively high speed, is higher than the cut-off frequency in a time phase in which the heart moves at a relatively low speed.

8. The ultrasonic diagnosis apparatus according to claim 6, wherein said filter control means has a first mode for controlling said filtering means so that the cut-off frequency of said filtering means is sequentially varied in a first pattern and a second mode for controlling said filtering means so that the cut-off frequency of said filtering means is sequentially varied in a second pattern.

9. The ultrasonic diagnosis apparatus according to claim 8, further comprising input means for selecting one of the first and second modes.

10. The ultrasonic diagnosis apparatus according to claim 1, wherein the scanning means includes only linear circuits and the image forming means includes at least one non-linear circuit.

11. The ultrasonic diagnosis apparatus according to claim 3, wherein said image forming means includes a wave detector for detecting the filtered echo signals.

12. The ultrasonic diagnosis apparatus according to claim 3, wherein said image forming means includes a logarithmic compressing circuit.

13. The ultrasonic diagnosis apparatus according to claim 1, further comprising selector means for selecting one of a first state in which the echo signals are supplied from the scanning means to the image forming means through said sampling means and said filtering means and a second state in which the echo signals are supplied from the scanning means directly to the image forming means.

14. The ultrasonic diagnosis apparatus according to claim 13, further comprising selector control means for controlling the selector means so that the first state is selected in a period in which the echo signals in a region of interest are output from the scanning means, and the second state is selected in a period in which the echo signals in a region other than the region of interest are output from the scanning means.

15. The ultrasonic diagnosis apparatus according to claim 14, wherein a gain in the first state is controlled to be greater than a gain in the second state.

* * * * *